US010281461B2

(12) United States Patent
Lim

(10) Patent No.: US 10,281,461 B2
(45) Date of Patent: May 7, 2019

(54) MICROPARTICLES FOR ANALYZING BIOMOLECULES, METHOD FOR PREPARING SAME, KIT FOR ANALYZING BIOMOLECULES, AND METHOD FOR ANALYZING BIOMOLECULES USING THE KIT

(71) Applicants: INDUSTRY-ACADEMIC COOPERATION FOUNDATION, DANKOOK UNIVERSITY, Gyeonggi-do (KR); SPECIALTY LAB SOLUTION CO., LTD., Gyeonggi-do (KR)

(72) Inventor: Heung Bin Lim, Gyeonggi-do (KR)

(73) Assignees: INDUSTRY-ACADEMIC COOPERATION FOUNDATION, DANKOOK UNIVERSITY, Suwon-si, Gyeonggi-Do (KR); Specialty Lab Solution Bio Co., Suwon-si, Gyeonggi-Do (KR)

( * ) Notice: Subject to any disclaimer, the term of this patent is extended or adjusted under 35 U.S.C. 154(b) by 200 days.

(21) Appl. No.: 14/423,161

(22) PCT Filed: Aug. 26, 2013

(86) PCT No.: PCT/KR2013/007636
§ 371 (c)(1),
(2) Date: Feb. 23, 2015

(87) PCT Pub. No.: WO2014/030985
PCT Pub. Date: Feb. 27, 2014

(65) Prior Publication Data
US 2015/0219640 A1 Aug. 6, 2015

(30) Foreign Application Priority Data

Aug. 24, 2012 (KR) .................. 10-2012-0093169
Sep. 11, 2012 (KR) .................. 10-2012-0100539
Sep. 12, 2012 (KR) .................. 10-2012-0101054

(51) Int. Cl.
*G01N 33/543* (2006.01)
*G01N 33/552* (2006.01)
*G01N 33/58* (2006.01)
*G01N 33/544* (2006.01)

(52) U.S. Cl.
CPC ..... *G01N 33/54313* (2013.01); *G01N 33/544* (2013.01); *G01N 33/5434* (2013.01); *G01N 33/54326* (2013.01); *G01N 33/54393* (2013.01); *G01N 33/552* (2013.01); *G01N 33/582* (2013.01); *G01N 2446/20* (2013.01)

(58) Field of Classification Search
CPC ........... G01N 33/54313; G01N 33/544; G01N 33/582
See application file for complete search history.

(56) References Cited

U.S. PATENT DOCUMENTS

2010/0081130 A1   4/2010  Lee et al.
2011/0177619 A1*  7/2011  Metters ............... G01N 33/533
                                                        436/518

FOREIGN PATENT DOCUMENTS

KR    10-0869589 B1    11/2008
KR    10-1149418 B1     6/2012
WO       03/089906 A2  10/2003
WO    2005/015213 A1    2/2005
WO    2007/029980 A1    3/2007
WO    2010/060216 A1    6/2010

OTHER PUBLICATIONS

Tang et al., "Nanoparticle-Based Sandwich Electrochemical Immunoassay for Carbohydrate Antigen 125 with Signal Enhancement Using Enzyme-Coated Nanometer-Sized Enzyme-Doped Silica Beads", Analytical Chemistry, vol. 82, No. 4, published Feb. 15, 2010.*
Jang et al., "Characterization and analytical application of surface modified magnetic nanoparticles", Microchemical Journal, vol. 94, pp. 148-158, published Nov. 6, 2009.*
PubChem, "Silica", pp. 1-6, printed retrieved Mar. 15, 2017.*
Perez et al., "Detection of respiratory syncytial virus using nanoparticle amplified immuno-polymerase chain reaction", Analytical Biochemistry, vol. 410, pp. 141-148, published Nov. 25, 2010 (Year: 2010).*
Hui Shi et al., "Rhodamine B isothiocyanate doped silica-coated fluorescent nanoparticles (RBITC-DSFNPs)—based bioprobes conjugated to Annexin V for apoptosis detection and imaging," Nanomedicine: Nanotechnology, Biology, and Medicine, 3, pp. 266-272 (2007).
Do Won Hwang et al., "A Nucleolin-Targeted Multimodal Nanoparticle Imaging Probe for Tracking Cancer Cells Using an Aptamer," The Journal of Nuclear Medicine, vol. 51, No. 1, pp. 98-105 (2010).
Dianping Tang et al., "Magnetic bead-based fluorescence immunoassay for aflatoxin B1 in food using biofunctionalized rhodamine B-doped silica nanoparticles," The Analyst, 135, pp. 2661-2667 (2010).

(Continued)

*Primary Examiner* — Tracy Vivlemore
*Assistant Examiner* — Nam P Nguyen
(74) *Attorney, Agent, or Firm* — Enshan Hong; VLP Law Group LLP

(57) ABSTRACT

The present invention relates to microparticles for analyzing biomolecules, a biomolecule analysis kit comprising the microparticles, and a method for analyzing biomolecules using the analysis kit, the microparticles for analyzing biomolecules comprising: a core including at least one selected from among an optical expression substance, a metallic material, and a magnetic material; a silica coating layer formed on the core; and at least one binding means, linked to the silica coating layer, for binding to an analysis subject biomolecule, wherein the optical expression substance is a fluorescent or a luminescent.

3 Claims, 10 Drawing Sheets

(56) References Cited

OTHER PUBLICATIONS

Cho Young-Seok et al., "In vitro and in vivo imaging of colon cancer with cetuximala conjugated fluorescent magnetic nanoparticles," Gastroenterology (2007).

Search Report dated Jun. 15, 2015, in related European Patent Appl'n. No. 13831292.1.

Ji-Lai Gong et al., "Ag/SiO2 core-shell nanoparticle-based surface-enhanced Raman probes for immunoassay of cancer marker using silica-coated magnetic nanoparticles as separation tools," Biosensors and Bioelectronics, 2007.

Xichun Zhou et al., "Improving the Signal Sensitivity and Photostability of DNA Hybridizations on Microarrays by Using Dye-Doped Core-Shell Silica Nanoparticles," Analytical Chemistry, 2004.

G.H. Du et al., "Characterization and application of Fe3O4/SiO2 nanocomposites," Journal of Sol-Gel Science and Technology, 2006.

\* cited by examiner

MICROPARTICLES FOR ANALYZING BIOMOLECULES, METHOD FOR PREPARING SAME, KIT FOR ANALYZING BIOMOLECULES, AND METHOD FOR ANALYZING BIOMOLECULES USING THE KIT

TECHNICAL FIELD

The present invention relates to microparticles for rapidly and accurately analyzing biomolecules such as antibiotics or cancer cells, a method for preparing the same, a biomolecule analysis kit, and a method for analyzing biomolecules using the kit.

BACKGROUND ART

Socially, in view of the medical and health care field, it is very important to rapidly and accurately analyze biomatter such as antibiotics or cancer cells. For example, a biomolecule such as enrofloxacin is an antibiotic for use in the fluoroquinolone command that is widely applied to the treatment of humans and animals, and may cause various side effects of from weak to very severe cases according to its application field.

Due to danger to human health, the Food and Drug Administration (FDA) and the World Health Organization (WHO) have enforced regulation on the use of enrofloxacin while the European Union (EU) has established a maximum residue limit of enrofloxacin. Therefore, monitoring of such antibiotic residues in foods with care is important for human health.

So far, various apparatuses and methods, such as high pressure liquid chromatography (HPLC), liquid chromatography mass spectrometry (LC-MS), capillary electrophoresis, enzyme linked immunosorbent assay (ELISA), etc., have been developed for analyzing biomolecules. Among them, HPLC and LC-MS are the most sensitive analysis techniques, but analysis is labor and time intensive, requiring elaborate operations and pretreatments. ELISA, although providing rapid analysis results, is complex in process, and relatively poor in quantitative sensitivity.

DISCLOSURE

Technical Problem

Accordingly, the present invention has been made keeping in mind the above problems occurring in the prior art, and an object of the present invention is to provide a microparticle for the rapid and accurate analysis of a biomolecule, a method for preparing the same, a biomolecule analysis kit, and a method for analyzing a biomolecule using the kit.

Technical Solution

In accordance with an aspect thereof, the present invention provides a microparticle for analysis of a biomolecule, comprising: a core including at least one selected from among an optical expression substance, a metallic material, and a magnetic material; a silica coating layer formed on the core; and at least one binding means, linked to the silica coating layer, for binding to an analysis subject biomolecule, wherein the optical expression substance is a fluorescent or a luminescent.

In accordance with another aspect thereof, the present invention provides a kit for analysis of a biomolecule, comprising: a first microparticle comprising: a core including an optical expression substance or a metallic material; a silica coating layer formed on the core; and a first binding means, linked to the silica coating layer, for binding specifically to the biomolecule to be analyzed, and a second microparticle comprising: a core including a magnetic material; a silica coating layer formed on the core; and a second binding means, linked to the silica coating layer, for non-specifically binding to the biomolecule to be analyzed.

In accordance with a further aspect thereof, the present invention provides a method of preparing a microparticle for analysis of a biomolecule, comprising: forming a core including at least one selected from among an optical expression substance, a metallic material, and a magnetic material; and coating the core with a silica coating layer.

In accordance with a still further aspect thereof, the present invention provides a method for analysis of a biomolecule, comprising: preparing a first microparticle including a first binding means that binds specifically to the analysis subject biomolecule; preparing a second microparticle including a second binding means that binds non-specifically to the analysis subject biomolecule; and mixing the first microparticle and the second microparticle with the analysis subject biomolecule, wherein the first microparticle includes an optical expression substance or a metallic material, and the second microparticle includes a magnetic material.

Advantageous Effects

Capable of simultaneously performing isolation and quantitative analysis of an analysis subject biomolecule, the present invention is improved in terms of time and cost effectiveness, and can determine the existence and quantity of distributed biomolecules, rapidly and accurately.

BEST MODE

Figure 1:
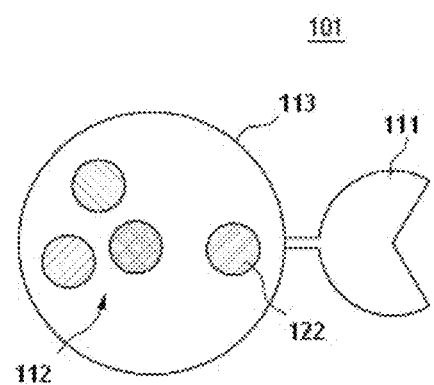
FIG. 1 is a schematic view showing the structure of a microparticle for analyzing a biomolecule in accordance with an exemplary example of the present invention.

The invention will now be described more fully hereinafter with reference to the accompanying drawings, in which exemplary embodiments of the invention are shown. The present invention may, however, be embodied in many different forms and should not be construed as being limited to the embodiments set forth herein. Rather, these embodiments are provided so that this disclosure will be thorough and complete, and will fully convey the scope of the invention to those skilled in the art. The same reference numerals refer to similar elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that although the terms "first," "second," etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the nature of the present invention.

Below, a detailed description will be given of the present invention with reference to the drawings.

FIG. 1 is a schematic view showing the structure of a microparticle 101 for analyzing a biomolecule in accordance with an exemplary example of the present invention. Below, the microparticle 101 for analyzing a biomolecule in accordance with one exemplary embodiment of the present invention will be explained with reference to FIG. 1.

As can be seen in FIG. 1, the microparticle 101 for analyzing a biomolecule in accordance with an exemplary embodiment of the present invention comprises a core including an optical expression substance 112 and a magnetic material therein; a silica coating layer 113 formed on the core; and at least one binding means 111, linked to the silica coating layer 113, for binding to a biomolecule to be analyzed.

As used herein, the term "biomolecule" means a substance released or isolated from a bioorganism, and is intended to encompass not only a substance produced from a bioorganism but also a substance remaining in a bioorganism after introduction into the bioorganism. Within the scope of the biomolecule, antibiotics, nucleic acids, hormones, enzymes, cells, tumors, cancer cells, bacteria, viruses, and isolates therefrom may fall. Examples of the antibiotics include enrofloxacin, ciprofloxacin, salinomycin, penicillin, cephalosporin, monobactam, cabapenem, ampicillin, carboxypenicillin, neomycin, gentamicin, cephamycin, sisomicin, erythromycin, clarithromycin, vancomycin, teicoplanin, lycomycin, sulfathiazole, tetracycline, oxytetracycline, and sulfamerazine.

Designed to bind to a biomolecule of interest, the microparticle 101 for analyzing a biomolecule in accordance with an exemplary embodiment of the present invention can trace or isolate the biomolecule. The mode in which the microparticle 101 is associated with a biomolecule may be versatile. In one exemplary embodiment, a biomolecule may be tagged with the microparticle. In another exemplary embodiment, the microparticle may be included within a biomolecule.

The microparticle 101 for analyzing a biomolecule in accordance with an exemplary embodiment of the present invention comprises an optical expression substance 112. Information on the existence and/or quantity of an optical expression substance can be optically measured. In this context, the optical expression substance 112 may be a fluorescent or a luminescent.

For example, when the optical expression substance 112 is a fluorescent, UV exposure enables it to emit visual light at a specific wavelength, thus allowing for the identification of the existence and quantity of the microparticle 101. The fluorescent may be exemplified by fluorescein isothiocyanate (FITC), cyanine (Cy), and rhodamine B isothiocyanate (RhBICT).

When a luminescent is used as the optical expression substance 112, it may emit visual light upon contact with an illuminant liquid, allowing for the identification of the existence and quantity of the microparticle 101.

In accordance with another exemplary embodiment of the present invention, the core of the microparticle for the analysis of a biomolecule may include a metallic material.

A metallic material, when included in the core, enables the identification of the existence and quantity of the microparticle using an X-ray apparatus or inductively coupled plasma mass spectrometry (ICP-MS). Herein, various metallic materials that are possible to be optically detected can be applied. In addition, the intrinsic isotope mass that each metal has can be used for the detection. Further, since ICP-MS is of very highly detective sensitivity, it can enhance both detection speed and sensitivity of biomolecules when it is applied to the optical expression substance 112 composed of a metallic material.

For the metallic material, any metal on the Periodic Table can be utilized. Examples of the metal include, but are not limited to, titanium, lead, cadmium, and elements of the lanthanide series, such as lanthanum, cerium, praseodymium, neodymium, promethium, samarium, europium, gadolinium, terbium, dysprosium, holmium, erbium, thulium, ytterbium, and lutetium. In addition, the metallic material may be a metal oxide such as iron oxide ($Fe_3O_4$), silicon oxide ($SiO_2$), and titanium oxide ($TiO_2$), as well as metal elements. Further, quantum dots or gold nanoparticles may be employed.

In another exemplary embodiment, the metallic material may be a single metal atom or an aggregate of two or more metal atoms. For a single metal atom, an element of the lanthanide series is preferable. However, when the metallic material is composed only of a single metal atom, the detection sensitivity may be poor because of the small size of the single metal atom. Further, the small size may make it difficult to prepare a microparticle. Hence, an aggregate of a plurality of single metal atoms may be advantageous in terms of detection sensitivity and ease of preparation. In this regard, the aggregate of metal atoms may be composed of approximately $10^4$-$10^6$ atoms. In a preferred embodiment of the present invention, the metallic material may comprise $7.0 \times 10^4 (\pm 1.3 \times 10^3)$ lead atoms or $1.5 \times 10^5 (\pm 1.6 \times 10^3)$ cadmium atoms. When an aggregate of plural single metal atoms are included within the microparticle 101, ICP-MS can detect it with greatly improved sensitivity, thus allowing for the rapid and accurate analysis of the biomolecule.

The core may be composed of different materials. In one preferred embodiment of the present invention, the core may contain a combination of a metallic material and a fluorescent. Briefly, the core may be composed of a combination of lead and RTC, or a combination of cadmium and RhBICT. These combinations increase the detection sensitivity of biomolecules, without spectral interference. Since ICT-MS exhibits high detection sensitivity, an actual subject to be measured may be a metallic material, with the fluorescent serving just as a subsidiary means. In one exemplary embodiment, the concentration of a biomolecule can be obtained by measuring the metallic material with the aid of ICP-MS while a biomolecule tagged with the microparticle 101 can be traced by detecting the fluorescent.

In accordance with another exemplary embodiment of the present invention, the core may comprise two or more different fluorescents, two or more different luminescents, or two or more different metallic materials.

In one preferred embodiment, the core may be composed of two different fluorescents RTC and Cy, or three different fluorescents RTC, Cy, and RhBICT. In one exemplary embodiment of the present invention, the core may be composed of two different metals lead and cadmium, or three different metals lead, cadmium and cerium. As illustrated above, the core may include a variety of different fluorescents, luminescents, metallic materials, or combinations thereof within the size of the microparticle 101. Hence, the core may be measured for a plurality of optical properties using an optical apparatus such as ICP-MS. Because the plural optical properties measured can be analyzed individually, the microparticle 101 comprising the core can be used for analyzing plural different biomolecules. In one exemplary embodiment of the present invention, one kind of microparticle can be tagged to a plurality of different biomolecules that can correspond to one of the plural optical features that the materials of the core have, so that the microparticle can be utilized for detecting a plurality of different biomolecules.

The core may take a bead form. For example, one microparticle for the analysis of biomolecules may consist of one bead. In one exemplary embodiment of the present invention the core of the microparticle 101 may comprise a matrix on which a plurality of beads is distributed, taking a bead form in its entirety. The matrix may be a polymer resin, and the beads may be fluorescents, luminescents, metallic materials, or combinations thereof.

The microparticle 101 for analyzing a biomolecule in accordance with an exemplary embodiment of the present invention may comprise a magnetic material 122. The magnetic material 122 refers to a material that can move in the presence of a magnetic field. Like the optical expression substance 112, the magnetic material 122 may take a bead form. The magnetic material 122 may be configured to isolate the microparticle 101 or the microparticle 101-tagged biomolecule. That is, the magnetic material 122 is used for the enrichment of the microparticle 101 or the microparticle 101-tagged biomolecule, thereby increasing the detection sensitivity. By minimizing the interference of materials rather than the subject biomolecule, the detection sensitivity for the subject biomolecule can be improved. As used herein, the term "enrichment" means the separation of a specific material from surrounding other materials.

The microparticle 101 for analyzing a biomolecule in accordance with an exemplary embodiment of the present invention comprises a silica coating layer 113 applied to the optical expression substance 112 and the magnetic material 122. The silica coating layer 113 may be formed using a reverse microemulsion method. In addition, the silica coating layer 113 may be configured to cover both the optical expression substance 112 and magnetic material 122. In an exemplary embodiment, as shown in FIG. 1, the silica coating layer 113 is formed to have a circle shape entirely covering the optical expression substance 112 and the magnetic material 122. Although seen to have a constant thickness in FIG. 1, the silica coating layer 113 may be inhomogeneous in thickness. Also, it may be oval or polygonal, or may partially cover the optical expression substance 112 or the magnetic material 122, with the other portion remaining exposed.

As seen in FIG. 1, the optical expression substance 112 and the magnetic material 122 are disposed relatively internally while the silica coating layer 113 is responsible for the outer of the microparticle 101. In this context, the microparticle 101 may have a core-shell structure in which the optical expression substance 112 and the magnetic material 122 exist together as a core, with the silica coating layer 113 serving as a shell.

The silica coating layer 113 may be prepared form a transparent material. For example, silica coating layer 113 may be formed of silica. Being covered by the silica coating layer 113, the optical expression substance 112 and the magnetic material 122 of the microparticle 101 can be protected from various external factors so that the optical property of the optical expression substance 112 and the magnetism of the magnetic material 122 can be maintained. For example, the silica coating layer can prevent the photobleaching of the optical expression substance 112, for example, when it is a fluorescent, and the reduction of magnetism when a foreign substance is attached to the magnetic material 122. Therefore, the silica coating layer can improve the sensitivity for measurement and separation of the biomolecule.

In addition, the microparticle 101 may include various kinds of optical expression substance 112 and magnetic material 122. It may be very onerous to treat various kinds of optical expression substance 112 and magnetic material 122, separately. When various kinds of optical expression substance 112 and magnetic material 122 that may be included within the microparticle 101 are coated with a constant composition of silica coating layer 113, the microparticle 101 has a homogeneous surface and is thus easy to treat.

The microparticle 101 for analyzing a biomolecule in accordance with an exemplary embodiment of the present invention comprises a binding means 111 for binding to a biomolecule to be analyzed. Versatile is the mode in which the binding means may bind to a biomolecule. As mentioned above, the microparticle 101 may be tagged to a biomolecule in one exemplary embodiment or may be included in a biomolecule in another exemplary embodiment. The binding of the binding means 111 to a biomolecule may be specific or non-specific, as will be described in detail.

In addition, the binding means 111 may be constructed on the silica coating layer 113. In this regard, the binding means may be linked to the silica coating layer 113 via a chemical bond. When the binding means is linked to the silica coating layer 113, the microparticle may take a bead form with a protrusion therefrom. When various kinds of optical expression substance 112 and magnetic material 122 that may be included within the microparticle 101 are coated with a constant composition of silica coating layer 113, the formation of the binding means 111 on the silica coating layer 113 may be conducted in a uniform process, thereby advantageously making the process simple.

With the aid of the microparticle 101 for analyzing a biomolecule in accordance with an exemplary embodiment of the present invention, a biomolecule to be analyzed can be isolated and measured simultaneously, so that an improvement can be brought about in time and cost effectiveness. In addition, the existence and quantity of the distributed biomolecule can be detected rapidly, and accurately. In detail, compared to ELISA, the method is simpler with an improvement in detection limit and reliability. Further, the microparticle 101 can be captured or enriched using the magnetism of the magnetic material 122 to increase the detection sensitivity of the biomolecule to be analyzed.

Figure 2:
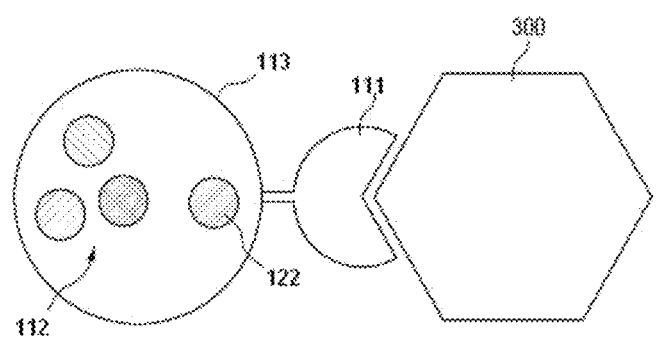
FIG. 2 is a schematic view showing the binding of a microparticle for the analysis of biomolecule to a biomolecule 300, which is an analysis subject, in accordance with another embodiment of the present invention.

FIG. 2 is a schematic view showing the binding of a microparticle 101 for the analysis of biomolecule to a biomolecule 300, which is an analysis subject, in accordance with another embodiment of the present invention. For the convenience of description, elements that function substantially the same roles in FIGS. 1 and 2 are assigned with the same reference numerals, and a description thereof will not be given repeatedly.

With reference to FIG. 2, the microparticle 101 for analyzing a biomolecule in accordance with an exemplary embodiment of the present invention comprises an optical expression substance 112, a magnetic material 122, and a binding means 111 for binding specifically to a biomolecule 300 to be analyzed.

The microparticle may comprise at least one binding means.

That is, a plurality of the binding means may be employed in the microparticle. The number of the binding means employed in the microparticle 101 may be adjusted according to the subject and field of application.

At least in part, the subject biomolecule 300 may be specifically bound by the binding means. As used herein the term "specifically binding" between the binding means and the analysis subject biomolecule 300 means that the binding means binds only to the analysis subject biomolecule 300. Hence, when the analysis subject biomolecule 300 and the microparticle 101 are mixed in a certain condition, the biomolecule 300 is associated with the microparticle 101 through a specific interaction with the binding means.

Examples of the specific interaction include antigen-antibody interaction, and complementary gene interaction.

For a biomolecule that has an epitope, by way of example, the binding means may include a specific antibody thereto. The antibody may be monoclonal or polyclonal. A monoclonal antibody is superior in terms of detection sensitivity not only because it is relatively small in size but also because it is much less prone to binding to a biomolecule that is not the analysis subject of interest. In one exemplary embodiment, the antibody may be a monoclonal antibody that binds specifically to an analysis subject biomolecule and which is less likely to interact with surrounding other molecules because of its small size.

When the biomolecule includes a polynucleotide, the binding means may be a complimentary, single-stranded polynucleotide. Herein, the single-stranded polynucleotide may be an oligonucleotide. Like a monoclonal antibody, an oligonucleotide is less prone to interaction with surrounding molecules because of its small size, thereby improving the detection sensitivity of the analysis subject biomolecule 300.

An experimental procedure of analyzing a biomolecule with the microparticles 101 for analyzing a biomolecule in accordance with an exemplary embodiment of the present invention will be briefly explained. First, the microparticle 101 is mixed in a sufficient amount with a biosample containing the analysis subject biomolecule 300 to allow the binding means of the microparticles 101 to bind specifically to the analysis subject biomolecule 300. Next, a device producing a magnetic field, for example, permanent magnet, may be used to capture the microparticles 101. Of the captured microparticles 101, biomolecule 300-bound microparticles may be separated by centrifugation due to the mass of the biomolecule.

Thereafter, the concentration of the analysis subject biomolecule 300 can be analyzed using an optical apparatus such as ICP-MS.

Figure 3:
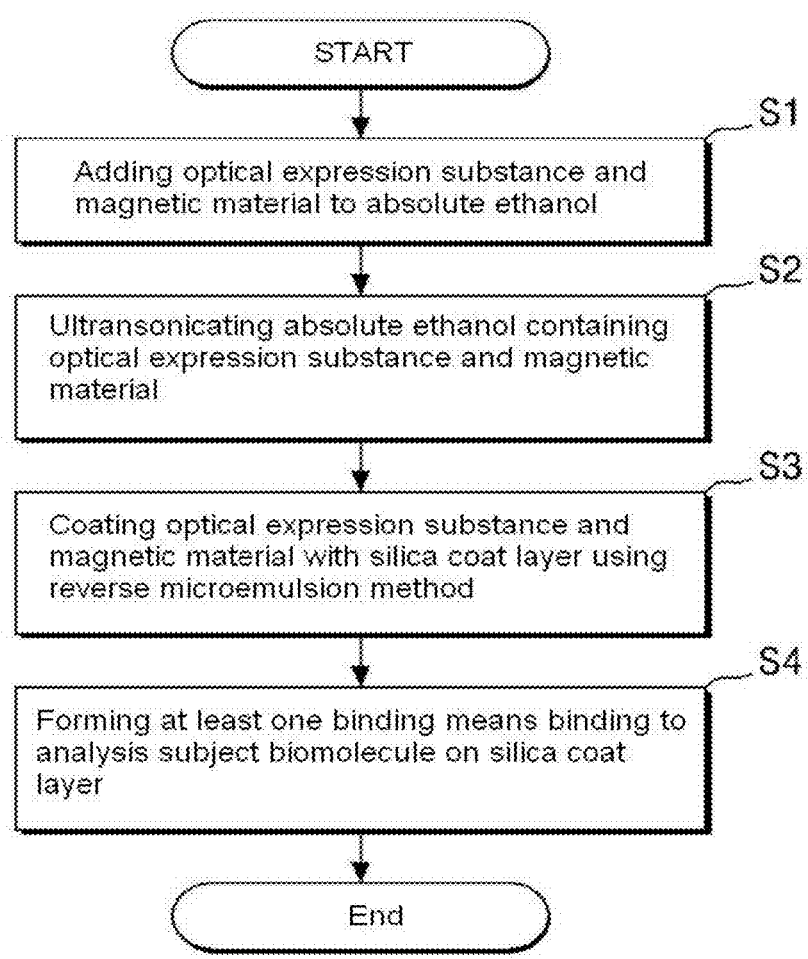
FIG. 3 is a flow chart illustrating a method of preparing a microparticle for the analysis of a biomolecule in accordance with an exemplary embodiment of the present invention.

FIG. 3 is a flow chart illustrating a method of preparing a microparticle for the analysis of a biomolecule in accordance with an exemplary embodiment of the present invention. With reference to FIG. 3, the method of preparing the microparticle 101 for analyzing a biomolecule in accordance with an exemplary embodiment of the present invention will be given. For the convenience of description, elements that function substantially the same roles in FIGS. 1 and 2 are assigned with the same reference numerals, and a description thereof will not be given repeatedly.

The method of preparing a microparticle for the analysis of biomolecules in accordance with the present invention comprises forming a core including at least one of an optical expression substance, a metallic material, and a magnetic material, and coating the core with a silica coating layer 130.

The formation of the core may be accomplished by placing optical expression substance, metallic material and magnetic material into absolute ethanol (S1), and ultrasonicating the absolute ethanol (S2). In one exemplary embodiment, metal chloride, for example, $CdCl_2$ or $PbCl_2$, a fluorescent, for example, RhBITC or RTC is mixed with a magnetic material, and subjected to ultrasonication. Thereafter, 3-aminopropyltriethoxysilane (APTEOS, 99%, Sigma-Aldrich. Co, USA) may be added and mixed in a light-tight condition.

The coating step may utilize a reverse microemulsion method (S3). In one exemplary embodiment, sodium docusate and water added to heptane and the solution is stirred. Then, the solution is added with the core and then with triethoxysilane (TEOS) and 25% ammonia, followed by stirring the solution in a light-tight condition. The microparticles 100 that are thus synthesized to have a core-shell structure may be separated by centrifugation. Thereafter, they are immersed in acetone and washed with ethanol before storage in deionized water.

After being formed, the microparticles for the analysis of biomolecules can be identified using ICP-MS, LIFM, scanning electron microscope (SEM), or CCD camera (Micro- Publisher 5.0, Q-Imaging). In one exemplary embodiment, when RTC or RhIBTC is employed as the optical expression substance of the microparticle, the optical expression substance can be excited using 473 nm DPSS (diode-pumped solidstate) laser (50 mW, BL473T-050, SLOG) or 563 nm He—Cd laser (3 mW, TriusEngineering, OK). The microparticle for the analysis of biomolecules may be generally spherical, with a diameter of 34 nm-38 nm, and specifically 36 nm.

In addition, the method of preparing a microparticle for the analysis of biomolecules in accordance with an exemplary embodiment of the present invention may further comprise forming on the silica coating layer at least one binding means that binds to a biomolecule to be analyzed (S4). As described above, the binding means may be specific or non-specific.

Figure 4:
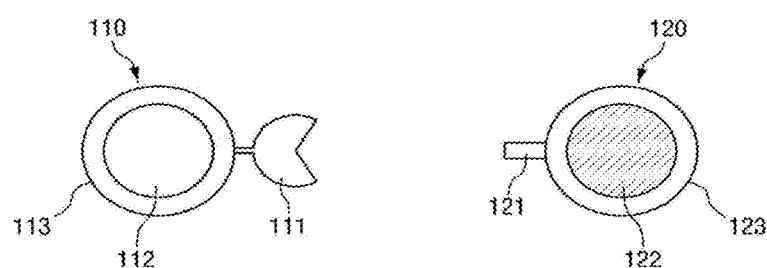
FIG. 4 is schematic view of a biomolecule analysis kit in accordance with one exemplary embodiment of the present invention.
Figure 5:
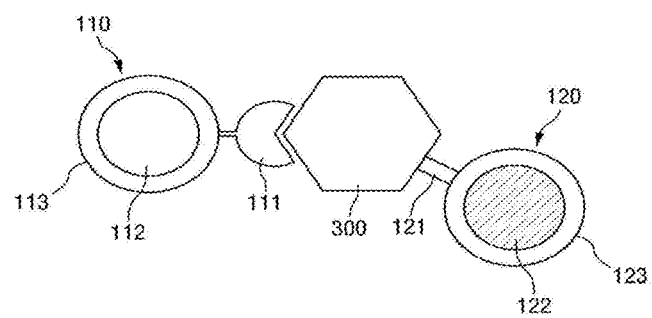
FIG. 5 is a schematic view showing binding relation between the biomolecule analysis kit according to one exemplary embodiment of the present invention and a biomolecule to be analyzed.

FIG. 4 is schematic view of a biomolecule analysis kit 100 in accordance with one exemplary embodiment of the present invention, and FIG. 5 is a schematic view showing binding relation between the biomolecule analysis kit according to one exemplary embodiment of the present invention and a biomolecule to be analyzed.

Below, the biomolecule analysis kit 100 in accordance with an exemplary embodiment of the present invention will be explained with reference to FIGS. 4 and 5.

As can be seen in FIG. 4, the biomolecule analysis kit 100 in accordance with an exemplary embodiment of the present invention comprises: a first microparticle 110 comprising: a core including an optical expression substance 112; a silica coating layer 113 formed on the core; a first binding means 111, linked to the silica coating layer 113, for binding specifically to a biomolecule to be analyzed, and a second microparticle 120 comprising: a core including a magnetic material 122; a silica coating layer 123 formed on the core; a second binding means 121, linked to the silica coating layer, for non-specifically binding to the biomolecule to be analyzed.

The first microparticle 110 may comprise at least a first binding means 111. The number of the binding means employed in the microparticle 110 may be adjusted.

At least in part, the subject biomolecule 300 may be specifically bound by the binding means. As used herein the term "specifically binding" between the binding means 111 and the analysis subject biomolecule 300 means that the binding means 111 binds only to the analysis subject biomolecule 300. Hence, when the analysis subject biomolecule 300 and the microparticle 110 are mixed in a certain condition, the biomolecule 300 is associated with the microparticle 110 through a specific interaction with the binding means 111.

Examples of the specific interaction include antigenantibody interaction, and complementary gene interaction.

For a biomolecule that has an epitope, by way of example, the first binding means 111 may include a specific antibody thereto. The antibody may be monoclonal or polyclonal. A monoclonal antibody is superior in terms of detection sensitivity not only because it is relatively small in size but also because it is much less prone to binding to a biomolecule that is not the analysis subject of interest. In one exemplary embodiment, the antibody may be a monoclonal antibody that binds specifically to an analysis subject biomolecule 300 and which is less likely to interact with surrounding other molecules because of its small size.

When the biomolecule includes a polynucleotide, the binding means 111 may be a complimentary, single-stranded polynucleotide. Herein, the single-stranded polynucleotide may be an oligonucleotide. Like a monoclonal antibody, an oligonucleotide is less prone to interaction with surrounding molecules because of its small size, thereby improving the detection sensitivity of the analysis subject biomolecule 300.

The core comprises an optical expression substance. Information on the existence and/or quantity of an optical expression substance can be optically measured. In this context, the optical expression substance 112 may be a fluorescent or a luminescent.

For example, when the optical expression substance 112 is a fluorescent, UV exposure enables it to emit visual light at a specific wavelength, thus allowing for the identification of the existence and quantity of the first microparticle 110. The fluorescent may be exemplified by fluorescein isothiocyanate (FITC), cyanine (Cy), and rhodamine B isothiocyanate (RhBICT).

When a luminescent is used as the optical expression substance 112, it may emit visual light upon contact with an illuminant liquid, allowing for the identification of the existence and quantity of the first microparticle 110.

In accordance with another exemplary embodiment of the present invention, the core of the microparticle for the analysis of a biomolecule may include a metallic material.

A metallic material, when included in the core, enables the identification of the existence and quantity of the microparticle using an X-ray apparatus or inductively coupled plasma mass spectrometry (ICP-MS). Herein, various metallic materials that are possible to optically detect can be applied. In addition, the intrinsic color that each metal has can be used for the detection.

The core may take a bead form. For example, the first microparticle may consist of one bead. In one exemplary embodiment of the present invention, the core of the first microparticle may comprise a matrix on which a plurality of beads is distributed, taking a bead form in its entirety. The matrix may be a polymer resin, and the beads may be fluorescents, luminescents, metallic materials, or combinations thereof.

In another exemplary embodiment of the present invention, the first microparticle 110 may further a coat layer 113 applied to the core. As illustrated in FIG. 4, the silica coating layer 113 is configured to cover the overall surface of the core in a bead form. Although seen to have a constant thickness, the silica coating layer 113 may be inhomogeneous in thickness. Also, it may partially cover the core, with the other portion remaining exposed.

The core is disposed relatively internally while the silica coating layer 113 is responsible for the outer of the microparticle. In this context, the first microparticle 110 may have a core-shell structure in which the optical expression substance 112 or the metallic material exist together as a core, with the silica coating layer 113 serving as a shell.

The silica coating layer 113 may be prepared form a transparent material. For example, silica coating layer 113 may be formed of silica. Being covered by the silica coating layer 113, the optical expression substance in the magnetic material can be protected from various external factors so that the optical expression substance or the magnetic material can maintain its intrinsic property. For example, the silica coating layer can prevent the photobleaching of the optical expression substance, for example, when it is a fluorescent. Therefore, the silica coating layer can improve the sensitivity for measurement and separation of the biomolecule.

In addition, the first microparticle 110 may include various kinds of optical expression substances or metallic materials. It may be very onerous to treat various kinds of optical expression substances or metallic materials, separately.

When various kinds of optical expression substances or magnetic materials that may be included within the first microparticle 110 are coated with a constant composition of silica coating layer 113, the microparticle 101 has a homogeneous surface so that the linking of a certain binding means to the silica coating layer 113 can be conducted in a uniform process, thereby simplifying the preparation process of the first microparticle 110.

As used herein, the term "non-specifically binding" of the second binding means 121 to the analysis subject biomolecule 300 means that the second binding means 121 may bind to a biomolecule that is not an analysis target, as well as to the analysis subject biomolecule 300. That is, the biomolecules bound by the second binding means 121 may include the analysis subject biomolecules 300 and/or the non-analysis subject biomolecules.

The second binding means 121 may be a functional group that can chemically bind to the analysis subject biomolecule 300. In other words, the second binding means 121 and the analysis subject biomolecule 300 can be chemically associated via a functional group. Examples of the functional group include an aldehyde group, an ether group, an ester group, a ketone group, a sulfide groups, a thiol group, an aryl group, an amine group, a carboxyl group, and a hydroxy group, with preference for an amine group, a carboxyl group and a hydroxy group thanks to their ability to form a bond with general biomolecules.

The second microparticle 120 may comprise at least one second binding means 121. The number of the binding means 121 employed in the second microparticle 120 may be adjusted.

The analysis subject biomolecule 300 may have a binding means corresponding to the second binding means of the second microparticle 120. The binding means of the biomolecule may be non-specifically associated with the second binding means 121. By way of example, an amide bond may be formed between the analysis biomolecule 300 and the second microparticle 120 when the functional group is an amine group and the analysis subject biomolecule 300 has a carboxyl group or when the functional group is a carboxylic group and the analysis subject biomolecule 300.

The second microparticle 120 may comprise a magnetic material 122. The magnetic material 122 refers to a material that can move in the presence of a magnetic field. The magnetic material 122 may take a bead form. The magnetic material 122 may be configured to isolate the second microparticle 120 or a conjugate of first microparticle 110-analysis subject biomolecule 300-second microparticle 120. That is, the magnetic material 122 is used for the enrichment of the second microparticle 120 or a conjugate of first microparticle 110-analysis subject biomolecule 300-second microparticle 120 in the solution containing the same, thereby increasing the detection sensitivity. As used herein, the term "enrichment" means the separation of a specific material from surrounding other materials.

The magnetic material 122 of the second microparticle 120 may be coated with the coat layer 123.

Like the first microparticle 110, the second microparticle 120 may have a core-shell structure. The coating layer 123 applied to the magnetic material 122 may be substantially the same as the coating layer 123 applied to the optical expression substance or the metallic material of the first microparticle 110. In detail, the coating layer 123 applied to the magnetic material 122 may be formed of the same material as that used for the coating layer 123 applied to the optical expression substance or the metallic material of the first microparticle 110. In addition, the optical expression substance or the metallic material, and the magnetic material 122 can be coated in the same process. Like the coated optical expression substance or metallic material, the magnetic material 122 of the second microparticle 120 can be protected from various external factors.

In addition, the first binding means 111 and the second binding means 121 may be switched to each other. That is, the first binding means 111 that specifically binds to the analysis subject biomolecule 300 may be linked to the particle including the magnetic material while the second binding means 121 that binds to the analysis subject biomolecule in a non-specific mode may be linked to the particle including the optical expression substance 112.

Figure 13:
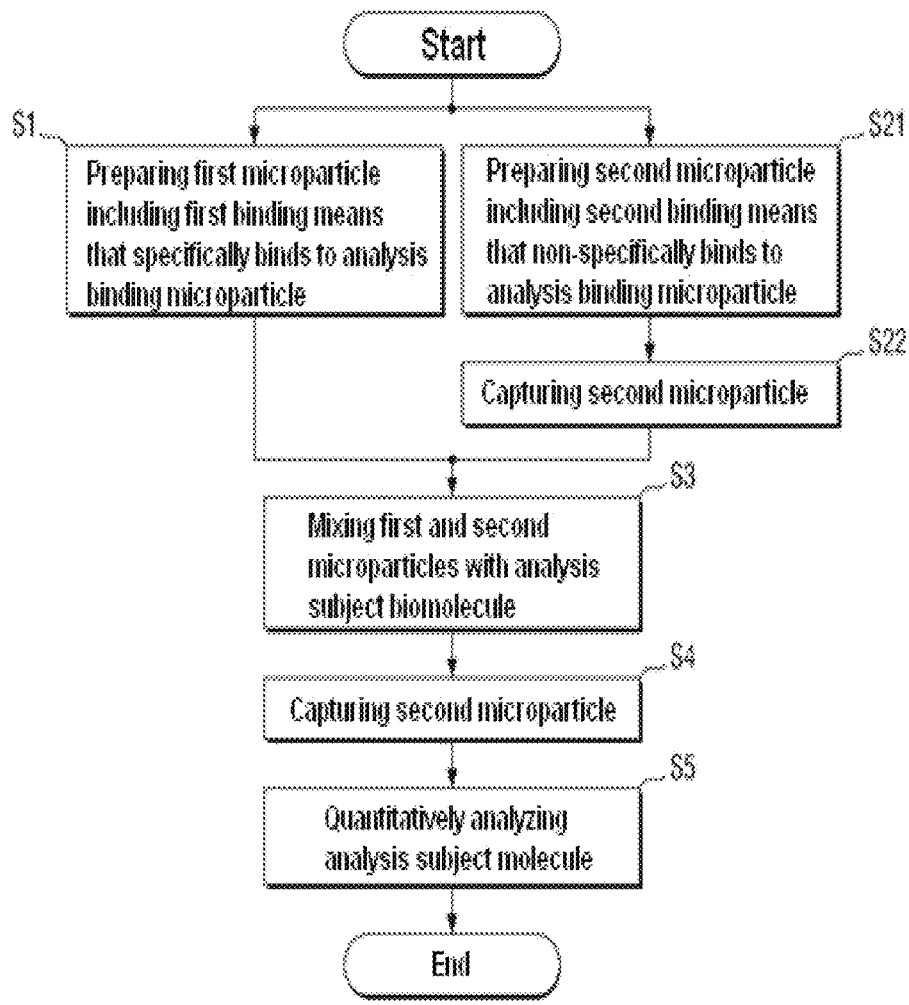
FIG. 13 is a flow chart illustrating a method of analyzing a biomolecule in accordance with an exemplary embodiment of the present invention.
Figure 14:
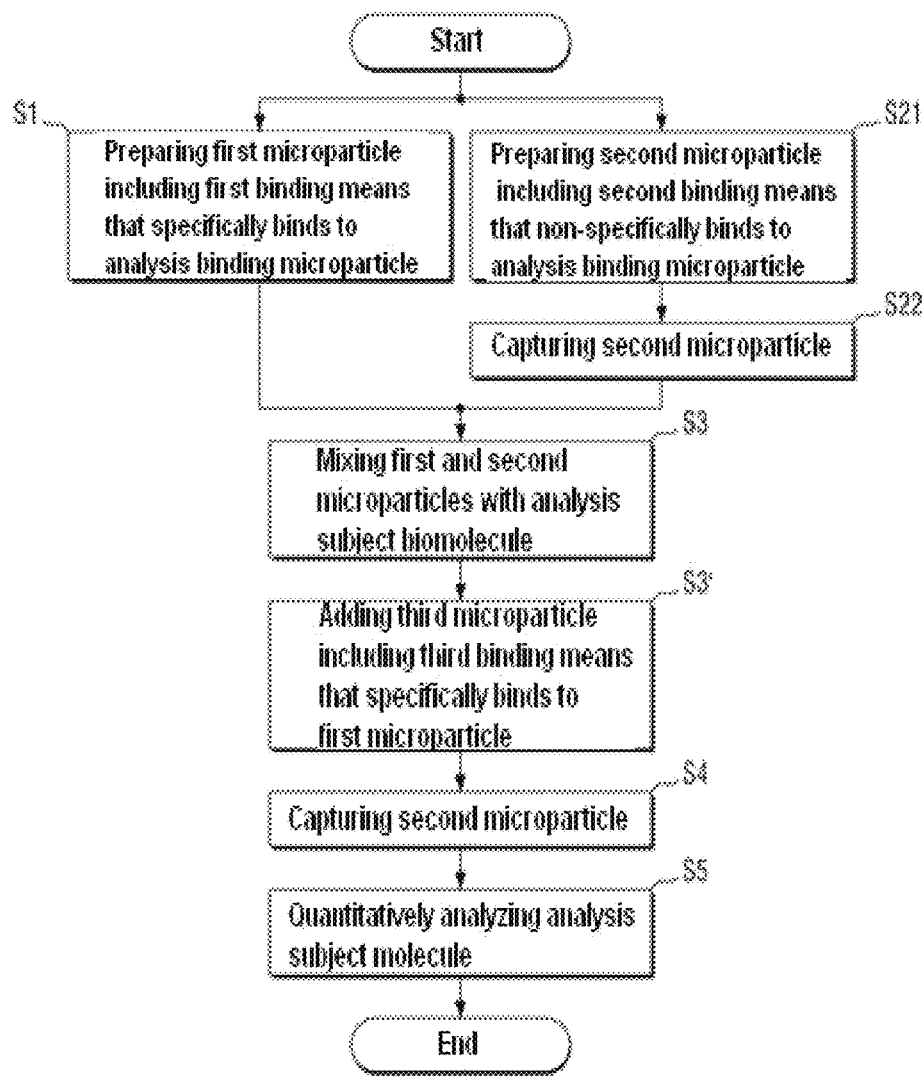
FIG. 14 is a flow chart illustrating a method of analyzing a biomolecule in accordance with another exemplary embodiment of the present invention.

FIG. 13 is a flow chart illustrating a method of analyzing a biomolecule in accordance with an exemplary embodiment of the present invention. Below, a description will be given of the biomolecule analyzing method, with reference to FIG. 13.

The method of analyzing a biomolecule in accordance with an exemplary embodiment of the present invention comprises preparing a first microparticle 110 including a first binding means 111 that specifically binds to an analysis subject biomolecule 300 (S1); preparing a second microparticle 120 including a second binding means 121 that binds to the analysis subject biomolecule 300 in a non-specifically mode (S21), and mixing the first microparticle 110 and the second microparticle 120 with the analysis subject biomolecule 300 (S3).

The first microparticle includes an optical expression substance or a metallic material while the second microparticle includes a magnetic material.

When the first microparticle 110 and the second microparticle 120 are mixed with the analysis subject biomolecule 300, the first binding means 111 of the first microparticle 110 specifically binds to the analysis subject biomolecule 300 while the second binding means 121 of the second microparticle 120 binds non-specifically to the same analysis subject biomolecule 300 to form a conjugate of the first microparticle 110—the analysis subject biomolecule 300—the second microparticle 120.

Herein, the number of the first binding means 111 included in the first microparticle 110 may be a factor important to the detection sensitivity and limit.

In order to measure the number of the first binding means 111 included in the first microparticle 110, the method may further comprise mixing and associating a third microparticle 230 including a third binding means that specifically binds to the first binding means 111 with the first microparticle 110, and measuring a ratio of association between the first microparticle 110 and the third microparticle 230 after the step of preparing a first microparticle 110 including a first binding means 111 that specifically binds to an analysis subject biomolecule 300 (S1).

Next, the third microparticle 230 and the third binding means 231 are explained with reference to FIG. 6 in which a biomolecule analysis kit 200 is structurally illustrated.

The third microparticle 230 may include an optical expression substance or a metallic material.

For the optical expression substance, a fluorescent or a luminescent may be used.

Unlike the optical expression substance 112 of the first microparticle 110, the optical expression substance 232 of the third microparticle 230 may not be coated with the coat layer 113. When the optical expression substance of the third microparticle is a luminescent, it does not need a coat because a luminescent has a generally stable structure.

Hence, the optical expression substance of the third microparticle may be tagged to the third binding means.

In addition, the optical expression substance 112 of the first microparticle and the optical expression substance 232 of the third microparticle 230 may absorb or reflect light with different respective wavelengths. That is, the optical expression substance 112 of the first microparticle and the optical expression substance 232 of the third microparticle may be different materials to each other.

The third binding means 231 may be an antibody that recognizes the first microparticle 110 as an antigen, or a single-stranded polynucleotide that complementarily binds to the first microparticle 110. For example, the third binding means may be a monoclonal antibody or an oligonucleotide, but is not limited thereto.

The number of the first binding means 111 that the first microparticle 110 has is measured. In this regard, first, the first microparticle 110 and the third microparticle 230 are mixed with each other to form a conjugate of the first microparticle 110 and the third microparticle 230. Next, when light having wavelengths that the optical expression substance 112 of the first microparticle 110 and the optical expression substance 232 of the third microparticle 230 respectively absorb or reflect is irradiated on a conjugate of the first microparticle 110 and the third microparticle, two calibration curves can be drawn. Comparison of the two calibration curves allows for indicating the number of the first binding means 111 that the first microparticle 110 includes.

The second microparticle 120 may include a magnetic material 122, and the method may further comprise capturing and enriching the second microparticle 120 (S22) after preparing a second microparticle 120 including a second binding means 121 that binds to the analysis subject biomolecule 300 in a non-specifically mode (S21). Only the second microparticle 120 can be selected and isolated out of a solution containing it.

In addition, the method may further comprise capturing and enriching the second microparticle 120 (S4) after mixing the first microparticle 110 and the second microparticle 120 with the analysis subject biomolecule 300 (S3). In this context, because the second microparticle 120 is associated with the analysis subject biomolecule 300 that is also bound by the first microparticle 110, the capture of the second microparticle 120 picks up a conjugate of the first microparticle 110—the analysis subject biomolecule 300—the second microparticle 120. That is, only a conjugate of the first microparticle 110—the analysis subject biomolecule 300—the second microparticle 120 can be fished out of the solution containing it.

Using a magnetic device, for example, a permanent magnet, an electrical magnet, etc., the second microparticle 120 can be captured. Both or either of the two steps of capturing the second microparticle 120 (S22, S4) may be conducted.

The enrichment of the conjugate of second microparticle 120 or first microparticle 110-analysis subject biomolecule 300-second microparticle 120 minimizes the interference of other materials, thus increasing the detection sensitivity for the analysis subject biomolecule.

After mixing the first microparticle 110 and the second microparticle 120 with the analysis subject biomolecule 300, the method may further comprise measuring a concentration of the analysis subject biomolecule 300 (S5). The concentration of the analysis subject biomolecule 300 can be analyzed by measuring the optical expression substance 112 of the first microparticle 110 with the aid of laser induced fluorescence microscopy (LIFM). In addition, the concentration of the analysis subject biomolecule 300 may be determined using a centrifuge method. Since a conjugate of the first microparticle 110—the analysis subject biomolecule 300—the second microparticle 120 has a large mass compared to the surrounding other materials, centrifugation can be utilized.

In addition, the concentration of the analysis subject biomolecule 300 may be measured using an X-ray apparatus or inductively coupled plasma mass spectrometry (ICP-MS).

The biomolecule analysis kit 100 according to an exemplary embodiment of the present invention can rapidly determine the existence and quantity of the distributed biomolecules. The existence and quantity of the distributed biomolecule can be detected accurately in a simple manner. In detail, compared to ELISA, the method is simpler with an improvement in detection limit and reliability. Further, the measurement of the number of the first binding means 111 included in the first microparticle 110, or the capture of the second microparticle 120 may increase the detection sensitivity of the biomolecule 300 to be analyzed.

Figure 6:
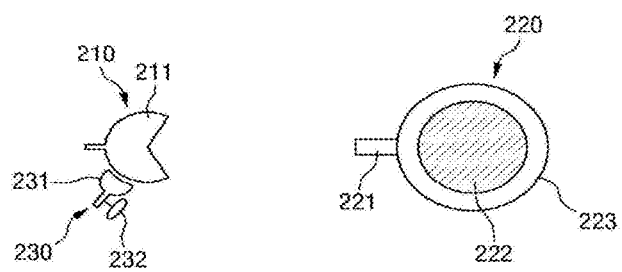
FIG. 6 is a schematic structural view of a biomolecule analysis kit according to another exemplary embodiment of the present invention.

FIG. 6 is a schematic structural view of a biomolecule analysis kit 200 according to another exemplary embodiment of the present invention. Below, explanation of the elements that are substantially the same as those of the biomolecule analysis kit 100 shown in FIGS. 1 and 2 is omitted.

Like the biomolecule analysis kit 100 according to an exemplary embodiment of the present invention, the biomolecule analysis kit 200 may comprise a first microparticle 210 including a first binding means 211 that specifically binds to an analysis subject biomolecule 300, and a second microparticle 220 including a second binding means 221 that non-specifically binds to the analysis subject biomolecule, and optionally a third microparticle 230 including a third binding means 231 that specifically binds to the first microparticle 210.

As described above, the second microparticle 220 may include a magnetic material 222 that may be coated with a silica coating layer 223. In addition, the third binding means 231 may be an antibody that recognizes the first microparticle 210 as an antigen, or a single-stranded polynucleotide that complementarily binds to the first microparticle 210.

In addition, the third microparticle 230 may include an optical expression substance or a metallic material wherein the optical expression substance 232 may be a fluorescent or a luminescent. Preferably, the third microparticle 230 may be tagged with a non-coated luminescent. Thus, the processes of coating the optical expression substance 232 with silica and linking a certain binding means to the coat layer can be omitted, so that the biomolecule analysis kit 200 can be further simplified.

Existence of the third binding means 231 including the optical expression substance may allow the first microparticle 210 to consist only of the first binding means 211. Hence, a linkage between the first binding means 211 and the optical expression substance 112 is unnecessary, which leads to simplifying the preparation of the first microparticle 210.

In another exemplary embodiment of the present invention, the method for analyzing a biomolecule may further comprise adding the third microparticle 230 including a third binding means 231 that specifically binds to the first microparticle 210 (S3') after mixing the first microparticle 110 and the second microparticle 120 with the analysis subject biomolecule 300 (S3).

Although the step of adding the third microparticle 230 including a third binding means 231 that specifically binds to the first microparticle 210 (S3') is further introduced, the biomolecule can be analyzed in a simpler process because the first microparticle 210 and the third microparticle 230 are structurally simple, as described above.

Figure 7:
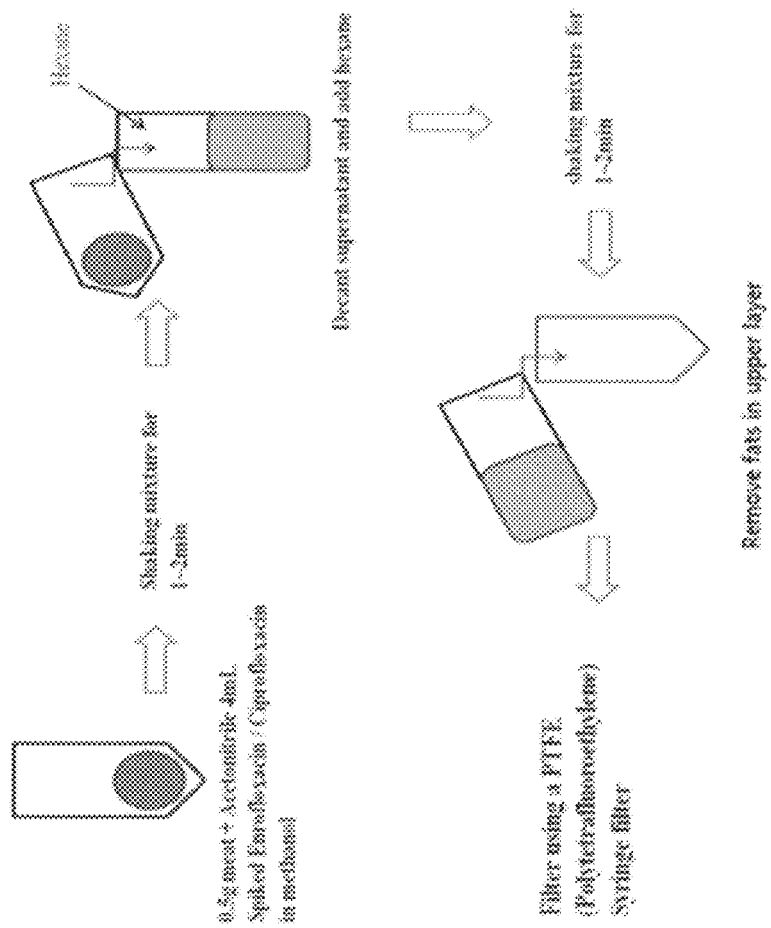
FIG. 7 is a schematic view illustrating a pre-treatment process of enrofloxacin and ciprofloxacin.
Figure 8:
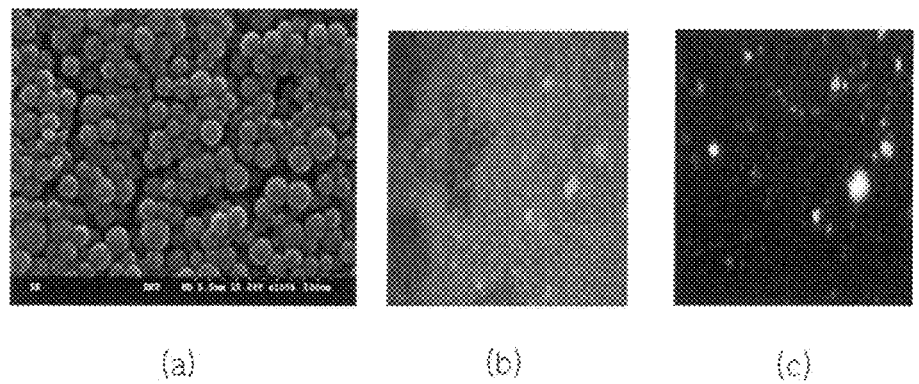
FIG. 8 shows fluorecein isothiocyanate-dopped core-shell nanoparticles in a scanning electron microscope image (a), a non-fluorescent image in the absence of laser (b), and a fluorescent image in the presence of laser (c).
Figure 9:
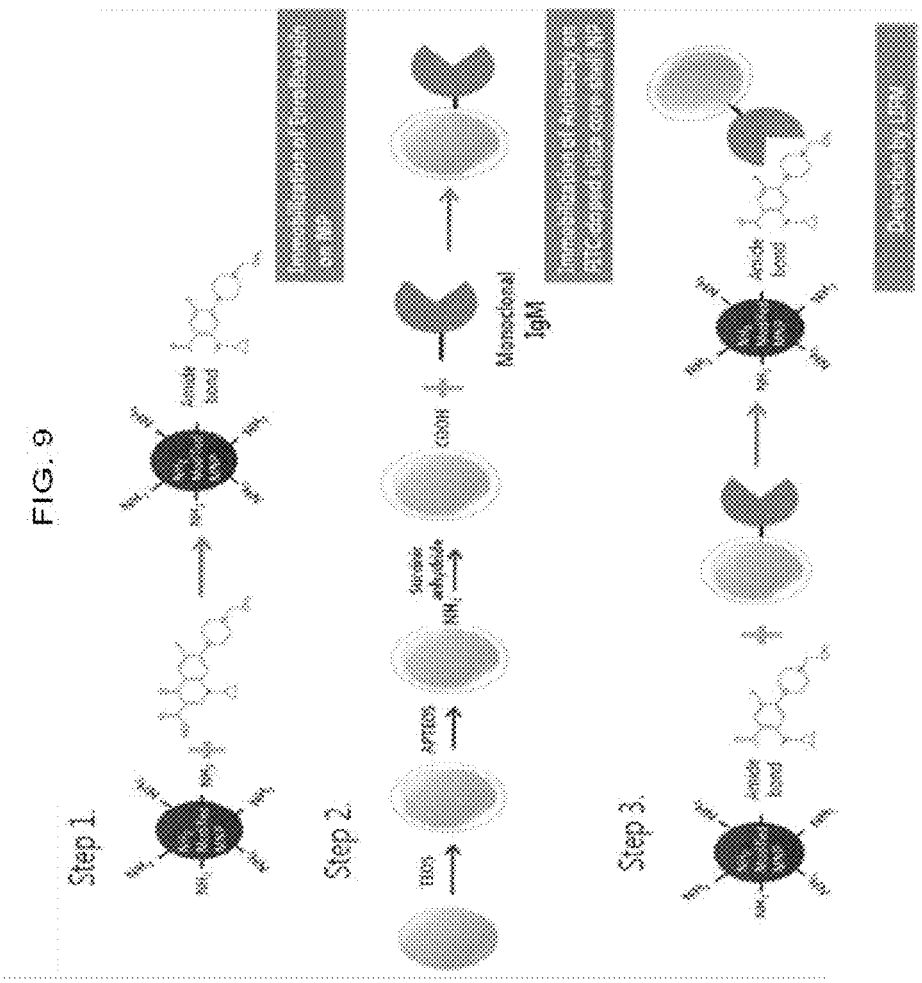
FIG. 9 is a schematic view illustrating an experimental procedure by which the biomolecule enrofloxacin is analyzed using the biomolecule analysis kit according to one exemplary embodiment.
Figure 10:
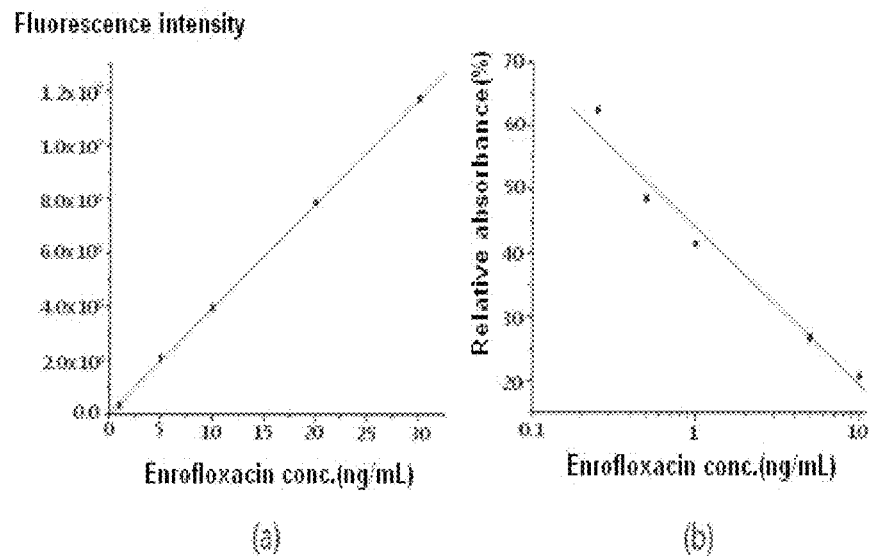
FIG. 10 shows calibration curves of enrofloxacin, drawn using the biomolecule analysis kit according to one embodiment of the present invention and laser induced fluorescence microscopy (a) and ELISA (b).
Figure 11:
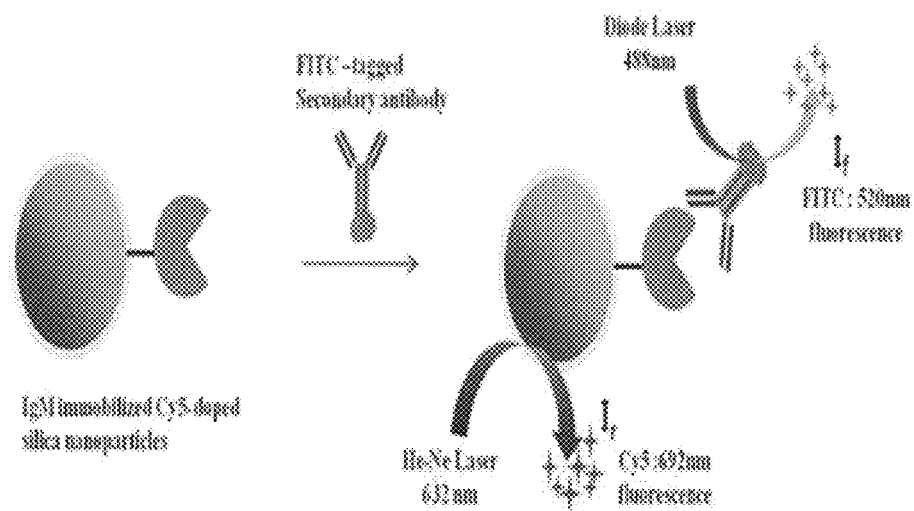
FIG. 11 is a schematic view illustrating the quantitative analysis of antibodies on the core-shell nanoparticles.
Figure 12:
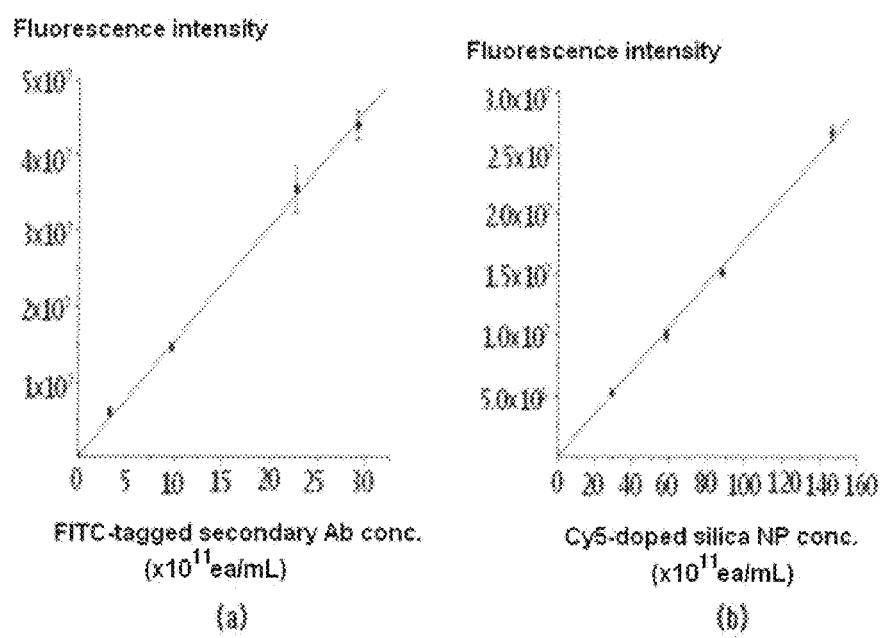
FIG. 12 shows calibration curves of a fluorescein isothiocyanate-tagged secondary antibody (a), and of cyanine-coated core-shell nanoparticles (b).

FIG. 7 is a schematic view illustrating a pre-treatment process of enrofloxacin and ciprofloxacin. FIG. 8 shows fluorecein isothiocyanate-dopped core-shell nanoparticles in a scanning electron microscope image (a), a non-fluorescent image in the absence of laser (b), and a fluorescent image in the presence of laser (c). FIG. 9 is a schematic view illustrating an experimental procedure by which the biomolecule enrofloxacin is analyzed using the biomolecule analysis kit 100 according to one exemplary embodiment. FIG. 10 shows calibration curves of enrofloxacin, drawn using the biomolecule analysis kit 100 according to one embodiment of the present invention and laser induced fluorescence microscopy (a) and ELISA (b). FIG. 11 is a schematic view illustrating the quantitative analysis of antibodies on the core-shell nanoparticles. FIG. 12 shows calibration curves of a fluorecein isothiocyanate-tagged secondary antibody (a), and of cyanine-coated core-shell nanoparticles (b).

Below, a detailed description will be given of Preparation Examples and Experimental Examples with reference to FIGS. 7 to 12.

MODE FOR INVENTION

Preparation Example 1: Preparation of Pre-Treated Enrofloxacin and Ciprofloxacin As illustrated in FIG. 7, 0.5 g of a meat sample was minced, and mixed with standard enrofloxacin (3-13 ng/mL, pH 6-7) and ciprofloxacin (3-13 ng/mL, pH 5-6). The sample was pre-treated with 4 mL of an acetonitrile (CH3CN) solvent, vortexed, and sonicated, followed by centrifugation to form a pellet. This pellet was treated with hexane (C6H14) to remove fats therefrom. After additional vortexing and ultrasonication, the supernatant was filtered through a 0.2 μm PTFE syringe filter to obtain pre-treated enrofloxacin and ciprofloxacin.

Preparation Example 2: Fabrication of Kit for Analyzing Enrofloxacin and Ciprofloxacin (1) Immobilization of Antibody onto FITC-Doped Core-Shell Nanoparticle A core of the RTC (fluorescein isothiocyanate, 90%, Sigma-Aldrich)-doped core-shell nanoparticles was synthesized using reverse microemulsion, after which the surface was modified as a silica shell. Since the stability of the core-shell nanoparticles has direct influence on the analysis performance, their size and distribution was controlled for quantitative analysis. The synthesized core-shell silica nanoparticles having a carboxyl group on the surface thereof was observed to have a diameter of 62.7±6.4 nm, as measured from 30 particles of the SEM (scanning electron microscopy) image of FIG. 8. The particles are relatively homogeneous and spherical. Visualization of green fluorescence with the aid of LIFM proved the existence of RTC in the core.

FITC-doped core-shell nanoparticles were functionalized with an amine group by reaction with 5 mM 3-(aminopropyl) triethoxysilane (APTEOS, 99%, Sigma-Aldrich). For immobilization, an antibody was functionalized with a carboxyl group at room temperature, using 0.01 g of succinic anhydride (99%, Sigma-Aldrich) in DMSO. After addition of 2 mL of acetone, centrifugation was conducted for 10 min at 4000 rpm to obtain FITC-doped core-shell nanoparticles as a pellet. Addition of 10 of IgM (obtained from human plasma, 95%, Abcam, UK) in PBS (phosphate-buffered saline) buffer (×10, Sigma-Aldrich) to the nanoparticles afforded the immobilization of the antibody to the FITC-doped, core-shell nanoparticles. To increase the immobilization efficiency, a carboxyl group was activated using a mixture of N-(3-dimethylaminopropyl)-N'-ethylcarbodiimide (EDC) and N-hydroxysuccinimide (NHS) (2:1) as a zero length cross linker. The immobilization of ciprofloxacin was performed in the same manner.

(2) Preparation of Amine-Conjugated, Core-Shell Magnetic Material

For Use in Selectively Extract an Antibiotic from a Standard or Spiked Sample solution, amine-functionalized magnetic material (size 4.5 μm, Dynabeads M-270 Amine, Invitrogen) was prepared. The magnetic material was coated with silica as mentioned above.

Preparation Example 3: Construction of Quantitative Analysis Kit with Antibody Immobilized to Core-Shell Nanoparticle Core-shell nanoparticles to which at least one antibody to enrofloxacin was conjugated were prepared in the same manner as in (1) of Preparation Example 2, with the exception that cyanine 5 (Cy5) was used instead of FITC. Meanwhile, a mixture of EDC and NHS (2:1) was added as a crosslinker to FITC, and incubated with 100 μl of a secondary antibody to the anti-enrofloxacin antibody for 2 hrs.

Briefly, 50 μl of Cy5-doped core-shell nanoparticles was reacted with 10 μl of IgM as an antibody to enrofloxacin. Then, 147 μl of FITC-tagged secondary antibody (Dylight 488, Abcam, UK) was added for conjugation, and unreacted antibodies were washed off with PBS.

Experimental Example 1: Quantitative Analysis of Enrofloxacin Using Pre-Treatment Sample of Preparation Example 1 and Analysis Kit of Preparation Example 2

As shown in FIG. 9, the pre-treated enrofloxacin sample obtained in Preparation Example 1 was reacted with the enrofloxacin analysis kit constructed in Preparation Example 2. The concentration of the enrofloxacin analysis kit was approximately twice that (30 ng/mL) of standard enrofloxacin. After reaction at room temperature for 1 hr, conjugated particles were collected using a permanent magnet, and washed with PBS buffer.

For visualization and quantitative fluorescent detection, lab-built LIFM and PMT (photomultiplier tube) equipped with a CCD camera (Micro Publisher 5.0, Q-Imaging) were used. The RTC that was doped to the core was excited using 473 nm DPSS laser (50 mW, BL473T-050, SLOC), with a 525±25 nm interference filter (FF02-525, Semrock) placed in front of PMT. The photons detected by PMT were counted using a photon counting system (C3866 and M8784, Hamamatsu).

With reference to FIG. 10, a detection limit of 54 pg/Ml (+3 pg/mL) was obtained from the calibration curve (a). In addition, the linear regression coefficient was calculated to be 0.9998. After optimization, mixing with 3-13 ng/mL reference enrofloxacin afforded a recovery of 78.1-103%.

Experimental Example 2: Quantitative Analysis of
Antibody on Core-Shell Nanoparticle Using
Analysis Kit of Preparation Example 3

Using the quantitative analysis kit constructed in Preparation Example 3, the antibody immobilized to the core-shell nanoparticles was quantitatively analyzed. With reference to FIG. 11, The measurement of Cy5 by LIFM was performed using 632.8 nm He—Ne laser as an excitation source, with a 692±25 nm interference filter installed for wavelength selection.

When the results were applied to the calibration curves of FIG. 12, each core-shell nanoparticle was calculated to have approximately 0.9 IgM immobilized thereto.

Comparative Example 1: Quantitative Analysis of
Antibody on Core-Shell Nanoparticle Enrofloxacin was detected using an ELISA kit (MaxSignal, BIOO Scientific, USA) according to the manufacturer's instruction. In each well, 50 µl of a standard or enrofloxacin-spiked sample and 100 µl of an antibody to enrofloxacin were mixed. After incubation at room temperature for 30 min, the well plates were washed and dried. Subsequently, 150 µl of an HRP (horseradish peroxidase)-conjugated antibody was added to each well and incubated at room temperature for 30 min. The enzymatic reaction was terminated with 100 µl of a stop buffer in each well. Absorbance was read at 450 nm on a microplate reader.

Returning to FIG. 10, a detection limit of 1.0 ng/mL (±0.1 ng/mL) was obtained from the calibration curve (b). In addition, the linear regression coefficient was calculated to be 0.974. After optimization, mixing with 3-13 ng/mL reference enrofloxacin afforded a recovery of 69.2-76.9%.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

DESCRIPTION OF THE REFERENCE
NUMERALS IN THE DRAWINGS 100, 200: biomolecule analysis kit
101: microparticle
110, 210: first microparticle
111, 211: first binding means
112, 232: optical expression substance
113, 123: coat layer
120: second microparticle
121: second binding means
122: magnetic material
230: third microparticle
231: third binding means
300: analysis subject biomolecule

The invention claimed is:

1. A kit for analysis of a biomolecule, comprising:
a first nanoparticle comprising:
   a core comprising a metallic material selected from the group consisting of lanthanum, cerium, praseodymium, neodymium, promethium, samarium, europium, gadolinium, terbium, dysprosium, holmium, erbium, thulium, ytterbium, lutetium, titanium, lead, cadmium, iron oxide ($Fe_3O_4$), silicon oxide ($SiO_2$), and titanium oxide ($TiO_2$);
   a silica coating layer formed on the core; and
   a first binding means, linked to the silica coating layer, for binding specifically to the biomolecule to be analyzed, and
a second nanoparticle comprising:
   a core comprising a magnetic material;
   a silica coating layer formed on the core; and
   a second binding means, linked to the silica coating layer, for non-specifically binding to the biomolecule to be analyzed, and
a third nanoparticle comprising a third binding means that specifically binds to the first binding means of the first nanoparticle and comprises a fluorescent substance or a luminescent substance,
wherein the metallic material is an aggregate of single metal atoms ranging in number from $10^4$ to $10^6$ atoms, and after use of the kit for an analysis, existence and quantity of the biomolecule are identified by an inductively coupled plasma mass spectrometry (ICP-MS),
wherein the core of the first nanoparticle further comprises a fluorescent material or a luminescent material,
wherein the fluorescent material is fluorescein isothiocyanate (FITC) or cyanine (Cy),
wherein the biomolecule is an enrofloxacin, the first binding means is an IgM, the second binding means is an amine group that forms a chemical bond with the biomolecule, and the third binding means is a secondary antibody to an anti-enrofloxacin antibody.

2. The kit of claim 1, wherein the chemical bond is an amide bond.

3. The kit of claim 1, wherein the core of the first nanoparticle comprises a combination of lead and fluorescein isothiocyanate (FITC).

* * * * *